United States Patent [19]

Burkard et al.

[11] 4,210,754
[45] Jul. 1, 1980

[54] MORPHOLINO CONTAINING BENZAMIDES

[75] Inventors: Willy Burkard, Reinach; Pierre-Charles Wyss, Muttenz, both of Switzerland

[73] Assignee: Hoffman-La Roche Inc., Nutley, N.J.

[21] Appl. No.: 953,721

[22] Filed: Oct. 20, 1978

Related U.S. Application Data

[63] Continuation of Ser. No. 764,621, Feb. 1, 1977, abandoned.

[51] Int. Cl.$^2$ .................. C07D 295/06; C07D 295/14
[52] U.S. Cl. .................................. 544/167; 544/169; 424/248.54
[58] Field of Search ............................... 544/167, 169

[56] References Cited

U.S. PATENT DOCUMENTS

| 3,502,623 | 3/1970 | Jucker et al. | 544/167 |
| 3,787,419 | 1/1974 | Bruce | 544/167 |

FOREIGN PATENT DOCUMENTS

| 45-32421 | 10/1970 | Japan . |
| 1170321 | 11/1969 | United Kingdom . |
| 1184047 | 3/1970 | United Kingdom . |

OTHER PUBLICATIONS

Chabrier et al. "Chem. Abstracts" vol. 51 (1957) p. 1187.
Kotelko et al. "Chem. Abstracts" vol. 79 (1973) No. 105,217K.
Morimoto et al. "Chem. Abstracts" vol. 75 (1971) No. 1,979w (Abstract of Japanese Patent 45 32421).

*Primary Examiner*—Henry R. Jiles
*Assistant Examiner*—R. W. Ramsuer
*Attorney, Agent, or Firm*—Jon S. Saxe; George M. Gould; Peter R. Shearer

[57] ABSTRACT

Benzamides of the formula

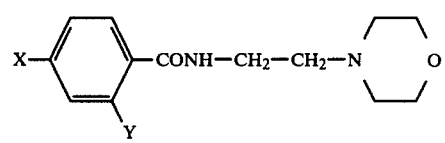

wherein X is halogen, trifluoromethyl or $C_{3-4}$-alkyl and Y is hydrogen, halogen or nitro, and N-oxides thereof, prepared inter alia from N-(2-aminoethyl)-morpholine and an acid of the formula

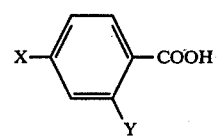

wherein X and Y are as hereinbefore set forth, are described. The end products are useful in the treatment of depressive conditions, that is, are useful as antidepressants.

7 Claims, No Drawings

MORPHOLINO CONTAINING BENZAMIDES

This is a continuation, of application Ser. No. 764,621 filed Feb. 1, 1977 now abandoned.

BRIEF SUMMARY OF THE INVENTION

The invention relates to benzamides characterized by the formula

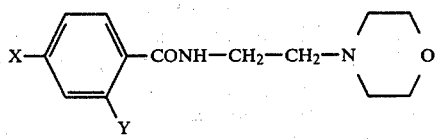

wherein X is halogen, trifluoromethyl or $C_{3-4}$-alkyl and
Y is hydrogen, halogen or nitro,
N-oxides or pharmaceutically acceptable acid addition salts thereof.

In another aspect, the invention relates to processes for the preparation of the compounds of formula I. In yet another aspect, the invention relates to pharmaceutical compositions containing the compounds of formula I.

DETAILED DESCRIPTION OF THE INVENTION

The benzamide derivatives of the invention are compounds characterized by the formula

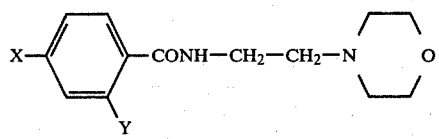

wherein X is halogen, trifluoromethyl or $C_{3-4}$-alkyl and Y is hydrogen, halogen or nitro,
and N-oxides and pharmaceutically acceptable acid addition salts thereof.

The term "halogen" denoted by X or Y, is chlorine, fluorine, bromine or iodine. $C_{3-4}$-alkyl is a straight-chain or branched-chain alkyl group containing 3 or 4 carbon atoms, namely n-propyl, isopropyl, n-butyl, isobutyl, 1-methylpropyl or t-butyl.

The compounds of formula I form addition salts with organic or inorganic acids at the nitrogen atom of the morpholino radical. Exemplary of such salts are hydrohalides, for example, hydrochlorides; phosphates; alkylsulfonates, for example, ethanesulfonates; monoarylsulfonates, for example, toluenesulfonate; acetates; citrates; benzoates and the like.

Preferred benzamides of formula I of the invention are those in which X is halogen. Also preferred are those benzamide derivatives in which Y is hydrogen or nitro.

The following are particularly preferred benzamide derivatives of this invention:
p-chloro-N-(2-morpholinoethyl)-benzamide,
p-fluoro-N-(2-morpholinoethyl)-benzamide,
p-bromo-N-(2-morpholinoethyl)-benzamide,
p-iodo-N-(2-morpholinoethyl)-benzamide, and
4-chloro-N-(2-morpholinoethyl)-2-nitrobenzamide.

Other preferred benzamide derivatives of this invention are:
α,α,α-Trifluoro-N-(2-morpholinoethyl)-p-toluamide,
p-t-butyl-N-(2-morpholinoethyl)-benzamide,
2,4-dichloro-N-(2-morpholinoethyl)-benzamide, and
p-chloro-N-(2-morpholinoethyl)-benzamide N'-oxide.

According to the process aspects of the present invention, the aforementioned benzamide derivatives, that is, the compounds of formula I, N-oxides and acid addition salts thereof, are prepared by (a) reacting N-(2-aminoethyl)-morpholine with an acid of the formula

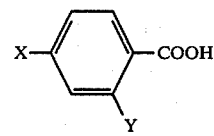

wherein X and Y are as hereinbefore described, or with a reactive functional derivative thereof, or (b) reacting morpholine with a compound of the formula

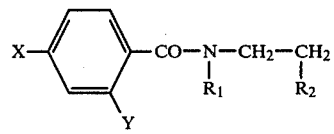

wherein X and Y are as hereinbefore described, $R_1$ is hydrogen and $R_2$ is halogen, or $R_1$ and $R_2$ taken together are an additional bond,
or (c) oxidizing a compound of the formula

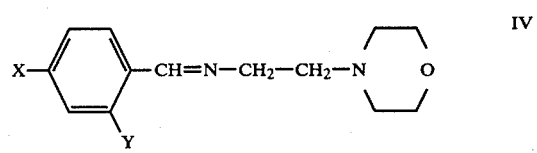

wherein X and Y are as hereinbefore described,
or (d) converting a thioamide of the formula

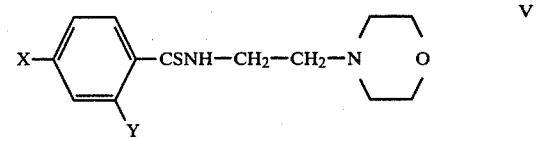

wherein X and Y are as hereinbefore described, into the corresponding amide, or (e) converting the grouping

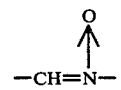

in a nitrone of the formula

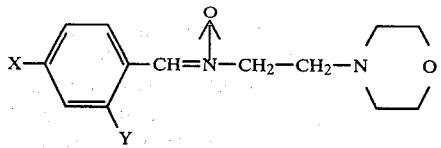

wherein X and Y are as hereinbefore described, into the grouping

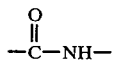

and, if desired, oxidizing a resulting compound of formula I to the corresponding N-oxide or converting a resulting compound of formula I into a pharmaceutically acceptable acid addition salt.

Examples of reactive functional derivatives of the acids of formula II are halides, for example, chlorides; symmetric or mixed anhydrides; esters, for example, methyl esters, p-nitrophenyl esters or N-hydroxysuccinimide esters; azides; and amides, for example, imidazolides or succinimides.

The reaction of N-(2-aminoethyl)-morpholine with an acid of formula II or a reactive functional derivative thereof according to process embodiment (a) can be carried out according to methods which are customary in peptide chemistry. Thus, for example, a free acid of formula II can be reacted with N-(2-aminoethyl)-morpholine in the presence of a condensation agent in an inert solvent. If a carbodiimide, for example, dicyclohexylcarbodiimide, is used as the condensation agent, the reaction is appropriately carried out in ethyl acetate, dioxane, methylene chloride, chloroform, benzene, acetonitrile or dimethylformamide at a temperature in the range of from about $-20°$ C. to about room temperature, preferably at about $0°$ C. If phosphorus trichloride is used as the condensation agent, the reaction is appropriately carried out in a solvent, such as, pyridine, at a temperature in the range of from about $0°$ C. to about the reflux temperature of the reaction mixture, preferably at about $90°$ C. In another aspect of process embodiment (a), N-(2-aminoethyl)-morpholine is reacted with one of the above-mentioned reactive functional derivatives of an acid of formula II. Thus, for example, a halide, such as the chloride, of an acid of formula II can be reacted with N-(2-aminoethyl)-morpholine in the presence of a solvent, such as, diethyl ether, pyridine or water, at about $0°$ C.

The compounds of formula III wherein $R_1$ is hydrogen and $R_2$ is halogen are N-(2-haloethyl)-benzamide, such as, p-chloro-N-(2-chloroethyl)-benzamide and the like. The compounds of formula III wherein $R_1$ and $R_2$ together are an additional bond are benzoylaziridines, such as, p-chloro-benzoylaziridine and the like.

According to process embodiment (b), morpholine can be reacted in a manner known per se with a compound of formula III at a temperature ranging up to the reflux temperature of the reaction mixture, if desired in the presence of a solvent. If a benzoylaziridine of formula III is utilized, the reaction is preferably carried out at the reflux temperature of the reaction mixture in the presence of an inert solvent, for example, toluene, acetone or benzene. If a N-(2-haloethyl)-benzamide of formula III is utilized, the reaction is preferably carried out at a temperature of about $100°$ C.

The oxidation of a compound of formula IV according to process embodiment (c) can be carried out in a manner known per se using an oxidizing agent, such as, hydrogen peroxide; potassium permanganate; an organic peracid, for example, peracetic acid; or a compound which releases hydrogen peroxide on solution in water, for example, an alkali metal peroxide or persulfuric acid. The oxidation is appropriately carried out in an inert solvent, for example, methanol, ethanol or acetone.

The conversion of a thioamide of formula V into the corresponding amide of formula I according to process embodiment (d) can be carried out in a manner known per se, for example, using lead tetraacetate in an inert solvent, such as water, at a temperature ranging up to reflux temperature of the reaction mixture, or also using 1,2-butylene oxide, if appropriate, in an inert solvent, for example, a lower alkanol, such as methanol, at a temperature ranging up to the reflux temperature of the reaction mixture.

The conversion of a nitrone of formula VI into a compound of formula I according to process embodiment (e) can be carried out in a manner known per se, for example, in the presence of acetic anhydride or acetyl chloride, if appropriate, in a solvent such as glacial acetic acid, at a temperature ranging up to the reflux temperature of the reaction mixture, preferably at about $90°$ C.

A compound of formula I can be converted in a manner known per se into the corresponding N-oxide using an oxidizing agent, such as, hydrogen peroxide; or a peracid, for example, peracetic acid, in a solvent, such as glacial acetic acid, at a temperature in the range of from about $0°$ C. to about $50°$ C., perferably at room temperature.

The starting materials of formula II, III, IV, V and VI are known or are analogs of known compounds and can be prepared by methods known per se.

The compounds of formula I, their N-oxides and pharmaceutically acceptable acid addition salts have monoamine oxidase (MAO) inhibiting activity. Due to this activity, the compounds of formula I, their N-oxides and pharmaceutically acceptable acid addition salts are useful in the treatment of depressive conditions. Stated another way, the compounds of formula I are useful as antidepressants.

The MAO inhibiting activity of the compounds of formula I of the invention can be determined using standard methods. Thus, the compounds of formula I to be tested were administered p.o. to rats. One hour thereafter the animals were killed and the MAO inhibiting activity in the liver homogenates was measured according to the method described in Biochem. Pharmacol. 12 (1963) 1439–1441. The activity thus determined of representative compounds of the present invention and their toxicity can be seen from the $ED_{50}$ values ($\mu$mol/kg.p.o. in rats) and $LD_{50}$ values (mg/kg, p.o. in mice) listed in the Table which follows:

TABLE

| Compound | $ED_{50}$ | $LD_{50}$ |
| --- | --- | --- |
| p-chloro-N-(2-morpholinoethyl)-benzamide | 5 | — |
| α, α, α-trifluoro-N-(2-morpholinoethyl)-p-toluamide | 16 | 1000–2000 |
| p-t-butyl-N-(2-morpholinoethyl)-benzamide | 16 | 1250–2500 |
| p-fluoro-N-(2-morpholinoethyl)-benzamide | 11 | 1250–2500 |
| p-bromo-N-(2-morpholinoethyl)-benzamide | 6 | 1250–2500 |
| p-iodo-N-(2-morpholinoethyl)-benzamide | 4 | 1250–2500 |
| 2,4-dichloro-N-(2-morpholinoethyl)- | | |

TABLE-continued

| Compound | ED$_{50}$ | LD$_{50}$ |
| --- | --- | --- |
| benzamide | 13 | 1250–2500 |
| 4-chloro-N-(2-morpholinoethyl)-2-nitrobenzamide | 2 | — |

The toxicity of p-chloro-N-(2-morpholinoethyl)-benzamide expressed in LD$_{50}$ (mg/kg, p.o. in rats) is 707±55 after 10 days.

The compounds of formula I, their N-oxides and their pharmaceutically acceptable acid addition salts can be used as medicaments in the form of pharmaceutical preparations which contain them in association with a compatible pharmaceutical carrier material. Such carrier material can be an organic or an inorganic inert carrier material which is suitable for enteral, for example oral, or parenteral administration, such as water, gelatin, gum arabic, lactose, starch, magnesium stearate, talc, vegetable oils, polyalkylene glycols, or the like. The pharmaceutical preparations can be made up in a solid form, for example, as tablets, dragees, suppositories or capsules, or in a liquid form, for example, as solutions, suspensions or emulsions. The pharmaceutical preparations may be sterilized and/or may contain compatible adjuvants such as preservatives, stabilizing agents, wetting agents, emulsifying agents, salts for modifying the osmotic pressure or buffering agents. They can also contain other therapeutic substances.

Appropriate pharmaceutical dosage forms contain from about 1 to 100 mg. of a compound of formula I, an N-oxide thereof or a pharmaceutically acceptable acid addition salt thereof. Appropriate oral dosage ranges are from about 0.1 mg/kg per day to about 5 mg/kg per day. Appropriate parenteral dosage ranges are from about 0.01 mg/kg per day to about 0.5 mg/kg per day. These ranges can be varied upwards or downwards, depending on the individual requirements and the directions of the attending physician. Oral administration is preferred.

The Examples which follow further illustrate the present invention. All temperatures are in degrees Centigrade, unless otherwise stated.

EXAMPLE 1

Preparation of
p-chloro-N-(2-morpholinoethyl)-benzamide

35 G. of p-chlorobenzoyl chloride are added dropwise to a solution of 26 g. of N-(2-aminoethyl)-morpholine in 200 ml. of pyridine, while stirring and cooling with ice-water. Thereafter, the mixture is stirred overnight at room temperature and subsequently evaporated to dryness. Then, the residue is evaporated twice more with 200 ml. of toluene each time. The solid residue is taken up in 300 ml. of ice-water and 300 ml. of methylene chloride and rendered basic with 3-N sodium hydroxide solution. The phases are separated and the methylene chloride extract is washed with water, dried over sodium sulfate and evaporated to dryness. The residue is recrystallized from isopropanol and 41.5 g. of p-chloro-N-(2-morpholinoethyl)-benzamide, melting point 137° C., are obtained.

The following compounds were prepared in an analogous manner:

α,α,α-trifluoro-N-(2-morpholinoethyl)-p-toluamide, melting point 120° C. to 121° C.;

p-t-butyl-N-(2-morpholinoethyl)-benzamide, melting point 94° C.;

p-fluoro-N-(2-morpholinoethyl)-benzamide, melting point 136° C. to 137° C.;

p-bromo-N-(2-morpholinoethyl)-benzamide, melting point 140° C. to 141° C.

p-iodo-N-(2-morpholinoethyl)-benzamide, melting point 160° C.;

2,4-dichloro-N-(2-morpholinoethyl)-benzamide, melting point 120° C.

EXAMPLE 2

Preparation of
p-chloro-N-(2-morpholinoethyl)-benzamide hydrochloride

13 G. of N-(2-aminoethyl)-morpholine are added dropwise to a solution of 17.5 g. of p-chlorobenzoyl chloride in 100 ml. of diethyl ether, with stirring and cooling with ice-water. After complete addition, the mixture is stirred for 2 hours at room temperature. The crystalline product is removed by filtration and washed with diethyl ether. 9.1 G. of p-chloro-N-(2-morpholinoethyl)-benzamide hydrochloride, melting point 207° C. to 208° C., are obtained after recrystallization from isopropanol.

4-Chloro-N-(2-morpholinoethyl)-2-nitrobenzamide hydrochloride, melting point 208° C., was prepared in an analogous manner.

EXAMPLE 3

Preparation of
p-chloro-N-(2-morpholinoethyl)-benzamide 10.5 G. of p-chlorobenzoic acid anhydride are added portionwise to a solution of 4.55 g. of N-(2-aminoethyl)-morpholine in 100 ml. of pyridine, with stirring and cooling with ice-water. After complete addition, the mixture is stirred overnight at room temperature and subsequently evaporated to dryness. The residue is then evaporated twice more with 100 ml. of toluene each time. The solid residue is taken up in 200 ml. of methylene chloride and 200 ml. of water and rendered basic with 3-N sodium hydroxide solution. The phases are separated and the methylene chloride extract is washed with water, dried over sodium sulfate and evaporated. The residue is recrystallized from isopropanol and 4.5 g. of p-chloro-N-(2-morpholinoethyl)-benzamide are obtained, which is identical to the product obtained in Example 1.

EXAMPLE 4

Preparation of
p-chloro-N-(2-morpholinoethyl)-benzamide 5.3 Ml. of chloroformic acid ethyl ester are added dropwise to a solution of 8.6 g. of p-chlorobenzoic acid and 7.6 ml. of triethylamine in 150 ml. of acetone, with stirring and cooling with ice-water. After one hour at 0° C., a solution of 6.5 g. of N-(2-aminoethyl)-morpholine in 50 ml. of acetone is added dropwise to the mixture and the mixture is then stirred overnight at room temperature. Thereafter it is concentrated, allowed to stand for 2 hours in the refrigerator and filtered. The filtrate is evaporated to dryness and the residue is taken up in 250 ml. of water and 250 ml. of methylene chloride. The phases are separated and the methylene chloride extract is dried over sodium sulfate and evaporated. The residue is recrystallized from isopropanol and 7.8 g. of p-chloro-N-(2-morpholinoethyl)-benzamide are obtained, which is identical to the product obtained in Example 1.

EXAMPLE 5

Preparation of p-chloro-N-(2-morpholinoethyl)-benzamide 8.2 G. of p-chlorobenzoic acid methyl ester and 6.25 g. of N-(2-aminoethyl)-morpholine are stirred together for 6 hours at 120° C. The mixture is then cooled to room temperature and 40 ml. of diethyl ether are added. Thereafter, the mixture is allowed to stand overnight in the refrigerator. The crystalline product is removed by filtration, washed with diethyl ether and recrystallized from isopropanol, and 2.6 g. of p-chloro-N-(2-morpholinoethyl)-benzamide are obtained, which is identical to the product obtained in Example 1.

EXAMPLE 6

Preparation of p-chloro-N-(2-morpholinoethyl)-benzamide 5.55 G. of p-chlorobenzoic acid p-nitrophenyl ester are added to a solution of 2.6 g. of N-(2-aminoethyl)-morpholine in 100 ml. of tetrahydrofuran and the mixture is allowed to stand overnight at room temperature. It is then evaporated to dryness and the residue is taken up in 200 ml. of methylene chloride. The methylene chloride solution is washed three times with 50 ml. of a 1% sodium hydroxide solution each time and twice with 50 ml. of water each time until neutral, dried over sodium sulfate and evaporated to dryness. The residue is recrystallized from isopropanol, and 3.1 g. of p-chloro-N-(2-morpholinoethyl)-benzamide are obtained, which is identical to the product obtained in Example 1.

EXAMPLE 7

Preparation of p-chloro-N-(2-morpholinoethyl)-benzamide 2.4 G. of N-(p-chlorobenzoyl)-succinimide are added to a solution of 1.3 g. of N-(2-aminoethyl)-morpholine in 100 ml. of dioxane and the mixture is stirred overnight at room temperature. The mixture is then evaporated to dryness. 50 Ml. of ice-water are added to the oily residue and the mixture which crystallizes is allowed to stand overnight in a refrigerator. The product is removed by filtration, washed with cold water, dried and recrystallized from isopropanol, and 0.65 g. of p-chloro-N-(2-morpholinoethyl)-benzamide is obtained, which is identical to the product obtained in Example 1.

EXAMPLE 8

Preparation of p-chloro-N-(2-morpholinoethyl)-benzamide 7.8 G. of p-chlorobenzoic acid and 6.5 g. of N-(2-aminoethyl)-morpholine are dissolved in 150 ml. of pyridine. 10.5 G. of dicyclohexylcarbodiimide are added at 4° C. and the mixture is stirred for 4 hours at 4° C. and overnight at room temperature. The mixture is then poured into 1 liter of water and the dicyclohexylurea formed is removed by filtration. The filtrate is extracted twice with 200 ml. of methylene chloride each time. The methylene chloride extract is dried over sodium sulfate and evaporated to dryness. The residue is recrystallized from isopropanol, and 0.6 g. of p-chloro-N-(2-morpholinoethyl)-benzamide is obtained, which is identical to the product obtained in Example 1.

EXAMPLE 9

Preparation of p-chloro-N-(2-morpholinoethyl)-benzamide 2.8 G. of phosphorus trichloride in 20 ml. of pyridine are added to 5.2 g. of N-(2-aminoethyl)-morpholine in 80 ml. of pyridine at −5° C. over a period of 15 minutes, with stirring. The mixture is stirred for 30 minutes at −5° C. and 90 minutes at room temperature. Then, 3.1 g. of p-chlorobenzoic acid are added and the mixture is heated for 3 hours at 90° C. This mixture is evaporated to dryness and the residue is evaporated twice more with 100 ml. of toluene each time. The solid residue is taken up in 100 ml. of methylene chloride and 100 ml. of ice-water and the mixture is rendered basic with 3-N sodium hydroxide solution. The phases are separated and the methylene chloride extract is washed with water, dried over sodium sulfate and evaporated. The residue is recrystallized from isopropanol and 1.3 g. of p-chloro-N-(2-morpholinoethyl)-benzamide are obtained, which is identical to the product obtained in Example 1.

EXAMPLE 10

Preparation of p-chloro-N-(2-morpholinoethyl)-benzamide 55.4 G. of p-chlorobenzoylaziridine and 26.5 g. of morpholine are boiled in 250 ml. of toluene for 2 hours under reflux. The solution is then cooled to room temperature, whereupon crystals separate out. The solution which crystallizes is allowed to stand overnight in a refrigerator. Thereafter, the product is removed by filtration, washed with toluene and recrystallized from isopropanol, and 75.9 g. of p-chloro-N-(2-morpholinoethyl)-benzamide are obtained, which is identical to the product obtained in Example 1.

EXAMPLE 11

Preparation of p-chloro-N-(2-morpholinoethyl)-benzamide 5.45 G. of p-chloro-N-(2-chloroethyl)-benzamide and 8.7 g. of morpholine are stirred together for 2 hours at 100° C. The mixture is cooled to room temperature and 50 ml. of water are added. Then, the mixture is rendered basic with 10% ammonia solution and extracted three times with 50 ml. of methylene chloride each time. The methylene chloride extract is dried over sodium sulfate and evaporated. The residue is chromatographed over a silica gel column with a mixture of chloroform and ethanol. The product is recrystallized from isopropanol, and 2.2 g. of p-chloro-N-(2-morpholinoethyl)-benzamide are obtained, which is identical to the product obtained in Example 1.

EXAMPLE 12

Preparation of p-chloro-N-(2-morpholinoethyl)-benzamide

26 G. of p-chlorobenzaldehyde and 24 g. of N-(2-aminoethyl)-morpholine are boiled in 150 ml. of benzene for 3 hours under reflux with water being separated. Then, the mixture is evaporated to dryness and the residue is distilled at 165° C./0.01 mmHg. 5 G. of the resulting 4-{2-[(p-chlorobenzylidene)-amino]-ethyl}-morpholine, 2.3 g. of sodium acetate and 3 ml. of 30% hydrogen peroxide are stirred in 60 ml. of methanol overnight at room temperature. Thereafter, the mixture is evaporated to dryness and the residue is taken up in 50 ml. of methylene chloride and 50 ml. of water. The phases are separated and the aqueous phase extracted with 50 ml. of methylene chloride. The methylene chloride extract is dried over sodium sulfate and evaporated. The residue is chromatographed over a silica gel column with a mixture of chloroform and ethanol. The pure fractions are combined and evaporated. The residue is recrystallized from isopropanol, and 0.7 g. of p-chloro-N-(2-morpholinoethyl)-benzamide is obtained, which is identical to the product obtained in Example 1.

EXAMPLE 13

Preparation of
p-chloro-N-(2-morpholinoethyl)-benzamide

900 Mg. of p-chloro-N-(2-morpholinoethyl)-thiobenzamide hydrochloride are boiled in 100 ml. of water with 2 g. of lead tetraacetate for 10 hours under reflux. The mixture is filtered and the filtrate is evaporated to dryness. The residue is chromatographed over a silica gel column with a mixture of chloroform and ethanol. The product is recrystallized from isopropanol, and 0.3 g. of p-chloro-N-(2-morpholinoethyl)-benzamide is obtained, which is identical to the product obtained in Example 1.

EXAMPLE 14

Preparation of
p-chloro-N-(2-morpholinoethyl)-benzamide 1.0 G. of p-chloro-N-(2-morpholinoethyl)-thiobenzamide hydrochloride is boiled in 100 ml. of methanol with 35 ml. of 1,2-butylene oxide for 14 hours under reflux. The mixture is evaporated to dryness. The residue is recrystallized from isopropanol, and 0.6 g. of p-chloro-N-(2-morpholinoethyl)-benzamide is obtained, which is identical to the product obtained in Example 1.

EXAMPLE 15

Preparation of
p-chloro-N-(2-morpholinoethyl)-benzamide 4.0 G. of α-(p-chlorophenyl)-N-(2-morpholinoethyl)-nitrone are heated to 90° C. in 15 ml. of glacial acetic acid and 15 ml. of acetic anhydride for 24 hours. The mixture is then cooled to room temperature, poured into 200 ml. of ice-water and rendered basic with 20% sodium hydroxide solution. Thereafter, the mixture is extracted twice with 100 ml. of methylene chloride each time. The methylene chloride extract is washed with water, dried over sodium sulfate and evaporated. The residue is chromatographed over a silica gel column with a mixture of chloroform and ethanol. The product is recrystallized from isopropanol, and 0.13 g. of p-chloro-N-(2-morpholinoethyl)-benzamide is obtained, which is identical to the product obtained in Example 1.

EXAMPLE 16

Preparation of
p-chloro-N-(2-morpholinoethyl)-benzamide N'-oxide

25 Ml. of 30% hydrogen peroxide are added to a solution of 10 g. of p-chloro-N-(2-morpholinoethyl)-benzamide in 50 ml. of glacial acetic acid and the mixture is allowed to stand for 48 hours at room temperature. Then, the mixture is evaporated to dryness and the residue chromatographed over a silica gel column with a mixture of chloroform and ethanol. The pure fractions are evaporated. The residue is recrystallized from an ethyl acetate/isopropyl ether mixture, and 6.8 g. of p-chloro-N-(2-morpholinoethyl)-benzamide N'-oxide, melting point 201° C. (decomposition), are obtained.

The following Example illustrates a typical pharmaceutical preparation utilizing a compound of the invention:

EXAMPLE A

Tablets of the following composition are prepared in a known manner:

| | | |
|---|---|---|
| p-chloro-N-(2-morpholinoethyl)-benzamide | 50 | mg. |
| Lactose | 95 | mg. |
| Maize starch | 100 | mg. |
| Talc | 4.5 | mg. |
| Magnesium stearate | 0.5 | mg. |
| Weight of one tablet | 250.0 | mg. |

We claim:
1. A compound of the formula

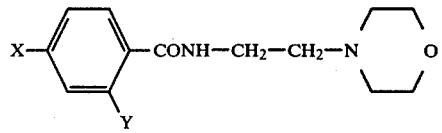

wherein X is halogen
and Y is hydrogen or nitro,
an N-oxide thereof or pharmaceutically acceptable acid addition salt thereof.

2. A compound in accordance with claim 1, p-chloro-N-(2-morpholinoethyl)-benzamide.

3. A compound in accordance with claim 1, p-iodo-N-(2-morpholinoethyl)-benzamide.

4. A compound in accordance with claim 1, p-fluoro-N-(2-morpholinoethyl)-benzamide.

5. A compound in accordance with claim 1, p-bromo-N-(2-morpholinoethyl)-benzamide.

6. A compound in accordance with claim 1, 4-chloro-N-(2-morpholinoethyl)-2-nitrobenzamide.

7. A compound in accordance with claim 1, p-chloro-N-(2-morpholinoethyl)-benzamide N'-oxide.

* * * * *